United States Patent
Gellert et al.

(10) Patent No.: US 10,126,277 B2
(45) Date of Patent: Nov. 13, 2018

(54) METHOD AND THERMAL CONDUCTIVITY DETECTOR

(71) Applicant: Siemens Aktiengesellschaft, Munich (DE)

(72) Inventors: Udo Gellert, Bellheim (DE); Glen Eugene Schmidt, Bartlesville, OK (US)

(73) Assignee: Siemens Aktiengesellschaft, Munich (DE)

( * ) Notice: Subject to any disclaimer, the term of this patent is extended or adjusted under 35 U.S.C. 154(b) by 261 days.

(21) Appl. No.: 15/151,069

(22) Filed: May 10, 2016

(65) Prior Publication Data

US 2016/0334376 A1     Nov. 17, 2016

(30) Foreign Application Priority Data

May 11, 2015   (DE) .......................... 10 2015 208 724
Sep. 15, 2015  (DE) .......................... 10 2015 217 662

(51) Int. Cl.
  *G01N 30/00* (2006.01)
  *G01N 30/62* (2006.01)
  (Continued)

(52) U.S. Cl.
  CPC .............. *G01N 30/62* (2013.01); *G01N 25/18* (2013.01); *G01N 27/18* (2013.01); *G01N 30/66* (2013.01);
  (Continued)

(58) Field of Classification Search
  CPC ........ G01N 30/62; G01N 30/66; G01N 25/18; G01N 27/18; G01N 27/0185;
  (Continued)

(56) References Cited

U.S. PATENT DOCUMENTS 3,733,463 A     5/1973  Low et al.
5,345,184 A *   9/1994  Andoh ................. G01N 27/185
                                        324/706
(Continued)

FOREIGN PATENT DOCUMENTS

CN     102667465    9/2012
CN     204065041   12/2014
JP     2000-146886  5/2000

OTHER PUBLICATIONS

Hongfei et al. "Design of Amplifier Circuit for Thermal Conductivity Detector in Micro Gas Chromatography," Chinese Journal of Chromatography, vol. 28, No. 8. Aug. 3, 2010.

*Primary Examiner* — Blake A Tankersley
(74) *Attorney, Agent, or Firm* — Cozen O'Connor

(57) ABSTRACT

A thermal conductivity detector includes a heatable resistive detector configured to be physically arranged in an analytes flow eluting from a chromatography column and electrically arranged with resistors in separate arms of a measuring bridge, an amplifier which detects differential voltage between two opposite nodes of the bridge and applies an output voltage to other opposite nodes of the measuring bridge to maintain the detector at a constant operating temperature, and an additional resistor with a controllable switch in parallel connected in series with the detector or resistor arranged in one arm of the bridge, where the switch is periodically turned on and off at a predetermined duty cycle and/or controlled by information on characteristic times-of-arrival of analytes at the detector to compensate for operating temperature uncertainties due to manufacturing variations of the resistors and/or to allow for processing small and large peaks of a chromatogram with highest available resolution.

10 Claims, 2 Drawing Sheets

(51) Int. Cl.
   *G01N 30/66*   (2006.01)
   *G01N 25/18*   (2006.01)
   *G01N 27/18*   (2006.01)
   *G01N 30/02*   (2006.01)

(52) U.S. Cl.
   CPC . *G01N 2030/025* (2013.01); *G01N 2030/621* (2013.01); *G01N 2030/625* (2013.01)

(58) Field of Classification Search
   CPC ....... G01N 2030/625; G01N 2030/025; G01N 2030/621
   See application file for complete search history.

(56) References Cited

U.S. PATENT DOCUMENTS

| | | | |
|---|---|---|---|
| 5,379,630 A * | 1/1995 | Lacey | G01N 27/185 324/105 |
| 5,587,520 A | 12/1996 | Rhodes | |
| 5,756,878 A | 5/1998 | Muto et al. | |
| 5,837,884 A * | 11/1998 | Kimura | G01N 27/18 73/25.04 |
| 2008/0291966 A1 | 11/2008 | Engel et al. | |
| 2012/0247184 A1* | 10/2012 | Kitanoya | G01N 27/18 73/25.05 |
| 2013/0133403 A1 | 5/2013 | Gellert et al. | |
| 2014/0020448 A1* | 1/2014 | Matsukura | G01N 33/0036 73/25.01 |
| 2014/0053631 A1* | 2/2014 | Watanabe | G01N 9/36 73/30.01 |
| 2017/0350841 A1* | 12/2017 | Chana | G01N 27/18 |

* cited by examiner

METHOD AND THERMAL CONDUCTIVITY DETECTOR

BACKGROUND OF THE INVENTION

1. Field of the Invention

The present invention relates to a thermal conductivity detector and method for operating the thermal conductivity detector.

2. Description of the Related Art

Thermal conductivity detectors are used to detect certain liquid or gaseous substances (fluids) based on their characteristic thermal conductivity, particularly in gas chromatography. Here, components or substances of a gas mixture are separated by passing a sample of a gas mixture in a carrier gas (mobile phase) through a separation column containing a stationary phase. The different components interact with the stationary phase that causes each component to elute at a different time, which is known as the retention time of the component. The separated substances, also referred to as analytes, are detected by a thermal conductivity detector which has a measuring cell with an appropriate detector element, e.g., an electrically heated filament disposed in a measurement channel. Depending on the thermal conductivity of the substance flowing past the heated filament, more or less heat is diverted from the heating filament to the wall of the measurement channel, and the heating filament is correspondingly cooled to a greater or lesser degree. As a result of the cooling of the heating filament, its electrical resistance changes, which is detected.

For this purpose and as known from, e.g., U.S. Pat. No. 5,756,878, the heating filament may be disposed in a measuring bridge, which contains additional resistors. The thermal conductivity of the substance passing the heating filament is obtained from an amount of energy that is supplied to the measuring bridge and controlled to maintain the temperature of the heating filament at a predetermined operating temperature. Instead of the resistors, further filaments may be provided that are fluidically parallel or in series with the filaments in the measurement channel and a reference channel, respectively.

From U.S. Pat. No. 5,379,630 or U.S. Pat. No. 5,587,520, it is known to provide two resistors and a controllable switch in one arm of a measuring bridge. Here, the switch is controlled to periodically change the resistance of the arm -between the values of the two resistors and thus alternately operate the heating filament at two different temperatures. The thermal conductivity of a substance flowing past the heated filament is determined from the difference of power dissipated by the filament at the two different operating temperatures.

U.S. Pat. No. 3,733,463 discloses a temperature control system that includes a modified Wheatstone bridge with a resistive-capacitive (RC) circuit in one arm of the bridge. The RC circuit includes a resistor that provides an effective resistance as a function of its absolute resistance and the on-time to off-time ratio of pulses supplied to a switch connected thereacross. A sawtooth voltage is produced across the RC circuit, where the voltage is compared with the voltage across a temperature sensor, and where heat is applied during each pulse period portion when the sawtooth voltage exceeds the voltage across the temperature sensor. As the Wheatstone bridge is powered from a DC battery, the operating temperature of the temperature sensor remains completely unaffected by the resistive-capacitive (RC) circuit.

The operating temperature of the heating filament is set by the ratios of the resistances in the measuring bridge. As the resistances are temperature dependent, it can be advantageous to use integrated, rather than discrete, resistors in a monolithic device. This provides the most stable measurement due to the cancellation of temperature effects, while the resistors are on the same substrate. However, a disadvantage of such a monolithic device is that manufacturing variances of the resistors do not provide a strong certainty of the exact operating temperature of the heating filament, or at the very least, a match in temperatures between successive thermal conductivity detectors, such as one in a measurement channel and another in a reference channel. Therefore, for practical use in, e.g., a gas chromatograph, the manufacturing variation of the monolithic devices requires adjustment of the resistance ratios.

Any effort to insert a variable resistor (potentiometer) or a compensating resistance is undesirable, both from a manufacturing perspective as well as from the potential addition of undesired noise and drift. A more advanced method would be laser trimming of the resistances. However, this is impractical for a micromachined (MEMS) device including the measurement channel with the filament, since the channel must be enclosed about the resistance elements, thus also closed to a laser trimming operation. The trimming operation would have to occur in an intermediate manufacturing step of the monolithic device, thus adding cost and value earlier in the process, thus running a higher risk of costly yield failures.

The thermal conductivity detector used in a gas chromatograph provides an output signal that represents a quantitative time domain spectrum of the composition of the gas mixture as a series of peaks (chromatogram). Each peak represents a component of the gas mixture, where the height and area of the peak determine the quantity of the component. The peaks can be very small and yet, within the same chromatogram, some peaks may be very large. For further digital processing, the chromatogram must be digitized, preferably with a high resolution of, e.g., 24 bit.

The quality of the measurement mainly reduces the signal to noise ratio of the complete measurement system as well as the resolution that is available in the analog to digital converter (ADC). It is obvious that in order to account for the largest peak, the resolution of the smaller peaks will be compromised. If, for example, a large peak is resolved with 100 steps, a 10 times smaller peak will be resolved with only 10 steps. Clearly the 100 step measurement is better defined than the 10 step measurement.

Thus, it might appear obvious to provide a variable electronic gain amplifier that increases the gain on the output signal of the thermal conductivity detector during periods where small peaks are expected. However, noise and wander effects are a significant challenge when performing chromatography and the variable gain amplifier would also amplify the noise and wander of the baseline of the chromatogram and thus only propagate the uncertainty of the measurement. Variable gain electronic systems also have a tendency to add noise and wander within the very bandwidth of the low frequency chromatogram. The chromatographic peak itself is Gaussian shaped, and the fidelity of this shape is important. Classic filtering of a noisy chromatogram, however, would distort the Gaussian shape.

SUMMARY OF THE INVENTION

In view of the foregoing, it is therefore an object of the invention to address the problem of manufacturing variances in a thermal conductivity detector without adding any extra manufacturing steps, extra hardware, or components that work against the desired low noise and low drift characteristics of the detector.

Another object is to allow for processing both small and large peaks of a chromatogram with highest resolution available but without amplifying or introducing noise. The "noise", referred to herein, is not just electrical in nature, but also includes artifacts of the detector, temperature control, flow effects, pressure, etc.

These and other objects and advantages are achieved in accordance with the invention by a thermal conductivity detector for a gas chromatograph comprising a heatable resistive detector element configured to be physically arranged in a flow of analytes eluting from a chromatography column and electrically arranged together with resistors in separate arms of a measuring bridge, an additional resistor with a controllable switch in parallel and connected in series with the detector element or resistor in one arm of the measuring bridge, an amplifier configured to detect a differential voltage between two opposite nodes of the measuring bridge and to apply an output voltage to the other opposite nodes of the measuring bridge in order to maintain the detector element at a constant operating temperature, and a control unit configured to provide a control signal to the switch for adjusting the operating temperature, where the control signal is a pulse-width modulated voltage with a period lower than the thermal time constant of the detector element.

It is also an object of the invention to provide a method for operating a thermal conductivity detector, where the method comprises passing a flow of analytes eluting from a chromatography column along a heatable resistive detector element that is electrically arranged together with resistors in separate arms of a measuring bridge powered by an amplifier that detects a differential voltage between two opposite nodes of the measuring bridge and applies an output voltage to the other opposite nodes of the measuring bridge to maintain the detector element at a constant operating temperature, and periodically turning an additional resistor in one arm of the measuring bridge on and off at a predetermined duty cycle and a period lower than the thermal time constant of the detector element to adjust the operating temperature of the detector element.

It is a further object of the invention to provide a gas chromatograph comprising at least one thermal conductivity detector.

The invention allows for dynamic adjustment of the operating temperature of the detector element (e.g., heating filament) to a desired value without a change in amplification or offset in the signal processing chain following the thermal conductivity detector, which inherently would add noise and wander effects.

By periodically turning the additional resistor on and off at a predetermined duty cycle and a period lower than the thermal time constant of the detector element, uncertainties in the operating temperature due to manufacturing variations of the resistances can be compensated accurately. The duty cycle may be determined in a one-time manufacturing calibration procedure and/or repeatedly in measurement calibration procedures when the detector element is exposed to only the carrier gas.

The invention further allows for dynamically changing the detector response based upon the expected peak signal without affecting the noise optimized amplifier and analog to digital converter.

For the detector element, it may be common for the constant operating temperature to be 130 to 140° C. while the gas chromatograph and sample gas to be within an oven is cooler in temperature, such as 60 to 80° C. This difference in temperature facilitates the thermal conductivity measurement and contributes strongly to the sensitivity. The invention advantageously allows for optimizing the constant operating temperature of the detector element to be high during small peaks and to be changed to a lower temperature during a large peak, so that the detector response is maximized for the subsequent ND conversion utilizing as much as the range of the A/D converter as is possible. To this end, the above-mentioned duty cycle is momentarily changed from one value to another value when predetermined ones of the analytes arrive at the detector element. Alternatively, if high-precision discrete resistors are used in the measuring bridge, thus not requiring compensation for manufacturing variations, the additional resistor is momentarily turned on each time a predetermined analyte arrives at the detector element. There are no additional elements in the signal chain (such as a gain element) that inherently would add noise and wander effects. Only the detector response is being manipulated, and the further signal processing remains unchanged with a fixed gain and associated ND converter, typically 24 bits that is performing with a SNR of 130 dB or better.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described by way of example and with reference to the accompanying drawing, in which.

DETAILED DESCRIPTION OF THE EXEMPLARY EMBODIMENTS

Figure 1:
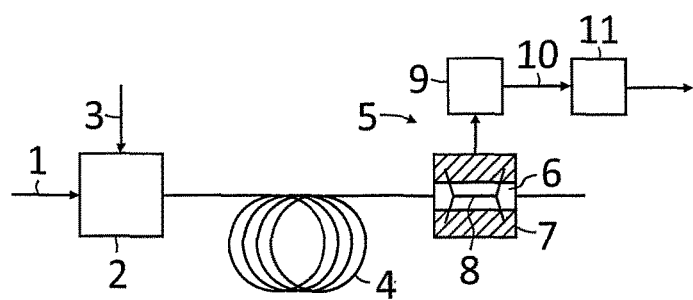
FIG. 1 is a simplified schematic block diagram of an exemplary gas chromatograph having a thermal conductivity detector in accordance with the invention.

FIG. 1 illustrates a gas chromatograph in which a carrier gas 1 is delivered to an injector 2, loaded there with a sample of a gas mixture 3 to be analyzed and subsequently introduced into a separation device 4 such as a single separation column or a complete system of separation columns. The separated components or substances of the gas mixture emerging successively from the separation device 4 travel to a thermal conductivity detector 5. There, the separated gas components are conveyed in a measurement channel 6 of a measuring cell 7 past a detector element 8, such as an electrically heated heating filament. Depending on the thermal conductivity of the gas components respectively flowing past in comparison with that of the carrier gas, more or less heat is transferred from the heating filament 8 to the channel wall such that the heating filament 8 is correspondingly cooled or heated. As a result, the electrical resistance of the heating filament 8 changes, where this change is detected in a detector circuit 9 of the detector 5. The analog output signal 10 of the thermal conductivity detector 5 indicates the presence and amount of the gas components passing the heating filament 8 and is supplied to a control and evaluation unit 11 for further processing.

Instead of a heating filament, which exhibits a positive temperature coefficient, a thermistor with a negative temperature coefficient may be used as the detector element 8.

Figure 2:
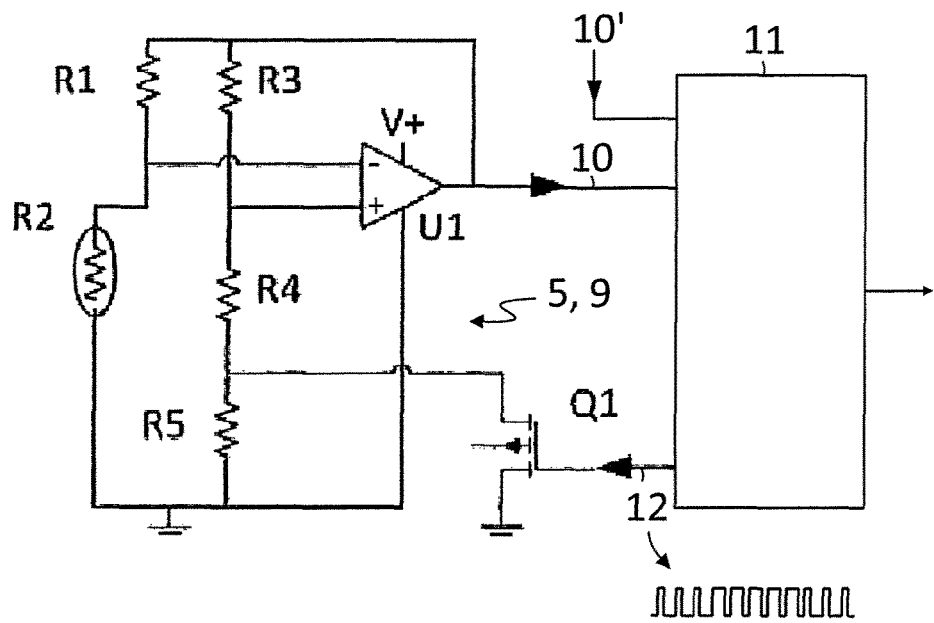
FIG. 2 is an exemplary embodiment of the thermal conductivity detector according to the invention.

FIG. 2 illustrates the thermal conductivity detector 5 with its detector circuit 9. A reference resistor R1 and the detector element 8, which is here denoted by R2, are arranged in one half of a measuring bridge (e.g., a Wheatstone bridge), and further resistors R3, R4, R5 are arranged in the other half. The measuring bridge (each of its halves) is excited by the output of a difference amplifier (operational amplifier) U1 that drives a voltage through the reference resistor R1 and onto the detector element R2 to control its resistance and, thus, its temperature. A voltage at the node between the reference resistor R1 and the detector element R2 is applied to either one of the inverting and non-inverting inputs of the amplifier U1, and a voltage at the node between the resistors R3 and R4 is applied to the other input of the amplifier U1. In the example shown, the difference amplifier 3 is configured for a detector element having a positive temperature coefficient (PTC) of resistance. In the case of a negative temperature coefficient (NTC) detector element, the inputs of the difference amplifier 3 have to be swapped. The amplifier U1 controls the current supplied to the detector element R2 such that the voltage generated at the connection point between the reference resistor R1 and the detector element R2 becomes equal to the voltage generated at the connection point between the resistors R3 and R4, thereby keeping the resistance value of the detector element R2 constant, such that R1/R2=R3/(R4+R5). As a result, the output voltage signal 10 of the detector circuit 9 is a measure of the voltage required to keep the detector element R2 at a certain operating temperature, and thus at a certain reference resistance, as a gaseous component that is mixed with the carrier gas flows across the detector element R2.

The output signal 10 of the thermal conductivity detector 5 is supplied to the control and evaluation unit 11 for further processing, including analog-to-digital conversion. The evaluation unit may comprise a precision difference amplifier circuit (not shown) for calculating a difference between the output signal 10 of the detector 5 and a reference signal 10' provided by a similar detector that is a measure of a voltage required to keep an identical detector element at the operating temperature with only the carrier gas. This results in a signal that measures the difference in the thermal conductivity in the various gases eluting from the gas chromatograph column with respect to the carrier gas. This difference signal is then digitized, preferably with a high resolution of, e.g., 24 bit with a signal-to-noise ratio (SNR) of 130 dB or better.

An additional resistor R5 with a controllable switch Q1 in parallel is arranged in one arm of the measuring bridge, here connected in series with the resistor R4 and referenced to signal ground as well as the detector element R2. The switch Q1 may be any type of electromechanical or semiconductor switching device, such as the FET transistor shown here. The switch Q1 is on/off controlled by a control signal 12 that is provided by the control and evaluation unit 11. The signal 12 is a pulse-width modulated (PWM) voltage with a period lower than the thermal time constant of the detector element R2.

As noted above, the ratio of R3 to R4 sets the operating temperature of the detector element R2. By adding element R5, now, when transistor Q1 is off, the ratio of R3 to (R4+R5) alters the operating temperature of the detector element R2. The PWM voltage 12 allows for accurately adjusting the resistance of the arm to any desired value between R4 and (R4+R5).

It further allows for maximizing the range of the output signal 10 for the analog-to-digital conversion by changing the PWM duty cycle from one value to another value based on information on characteristics and expected concentration ranges of the analytes and their times-of-arrival at the detector 5. If an upcoming peak in the chromatogram is expected to be small, the duty cycle of the PWM voltage 12 and thus the on/off duty of the switch Q1 is increased to set the operating temperature of the detector element R2 to a higher constant value, which makes the detector 5 more sensitive to the small peaks. If peaks in the chromatogram are expected to be large, the duty cycle of the PWM voltage 12 is decreased, thus setting the operating temperature of the detector element R2 to a lower constant value, which makes the detector 5 more respond with a smaller signal 10 to the already larger peak information.

In chromatographic practice, the quality of the components used is crucial. The ratios between R1, R3 and R4, or (R4+R5), respectively, must be precisely fixed, which is to say that these components must be extremely stable and must track each other within 0 to 2 ppm over all conditions (e.g., time or temperature) for a >130 dB SNR chromatography system. However, this no longer applies if a leakage current is considered for the switch Q1, which leakage current represents an effective resistance in parallel to the additional resistor R5. The problem with the leakage resistance is that a leakage current is not stable. It changes with time, temperature, mechanical stresses, etc., and also time dependency, thus being manifested as a noise/drift/wander component. In a FET transistor, this value can increase inexactly, but more or less logarithmically with temperature.

Figure 3:
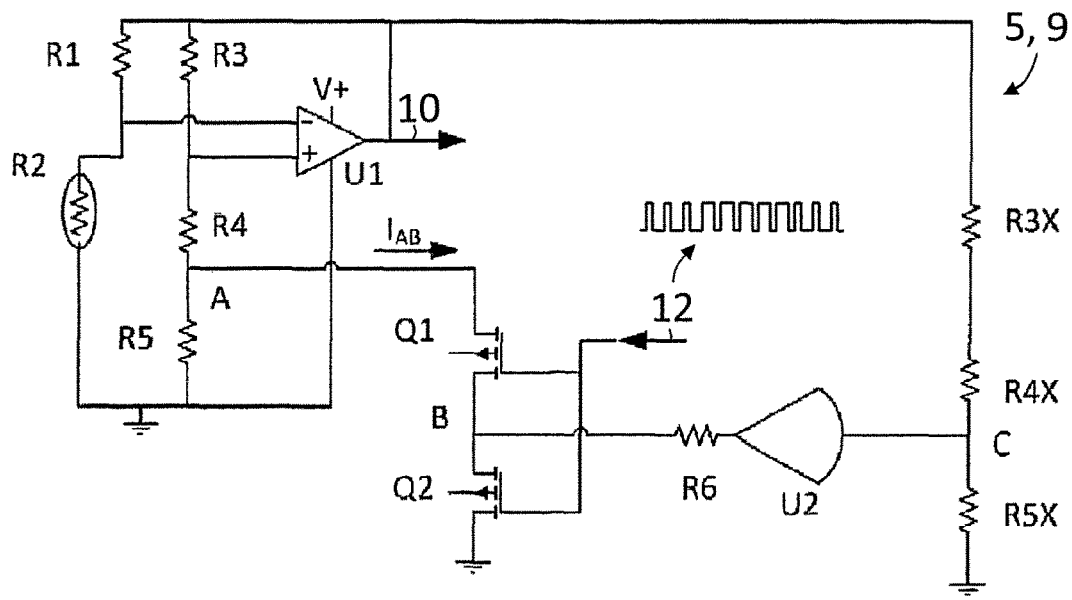
FIG. 3 is another exemplary embodiment of the thermal conductivity detector according to the invention.

FIG. 3 shows an advantageous modification of the thermal conductivity detector of FIG. 2 that compensates for such a leakage current IAB. Here, the controllable switch Q1 is in series with another switch Q2, and both switches Q1, Q2 are controlled together by the control signal 12 to enable the change in operating temperature of the detector element R2. A voltage divider with resistors R3X, R4X, R5X is connected between the output of the amplifier U1 and signal ground. These resistors R3X, R4X, R5X have identical ratios to the resistors R3, R4 and R5. A tap C of the voltage divider between R4X and R5X is coupled to a node B between the switches Q1 and Q2. While Q1 and Q2 are off, the leakage current IAB is now negligible because the voltages at the nodes A (between R4 and R5) and B (between Q1 and Q2) are at equal potentials due to a buffer amplifier (voltage follower) U2 that provides a unity gain from tap C, which tracks the voltage at node A. Any variances in R3X, R4X and R5X are insignificant, because the variance in potential from node A to B would such a low potential difference, even in the non-ideal case.

Figure 4:
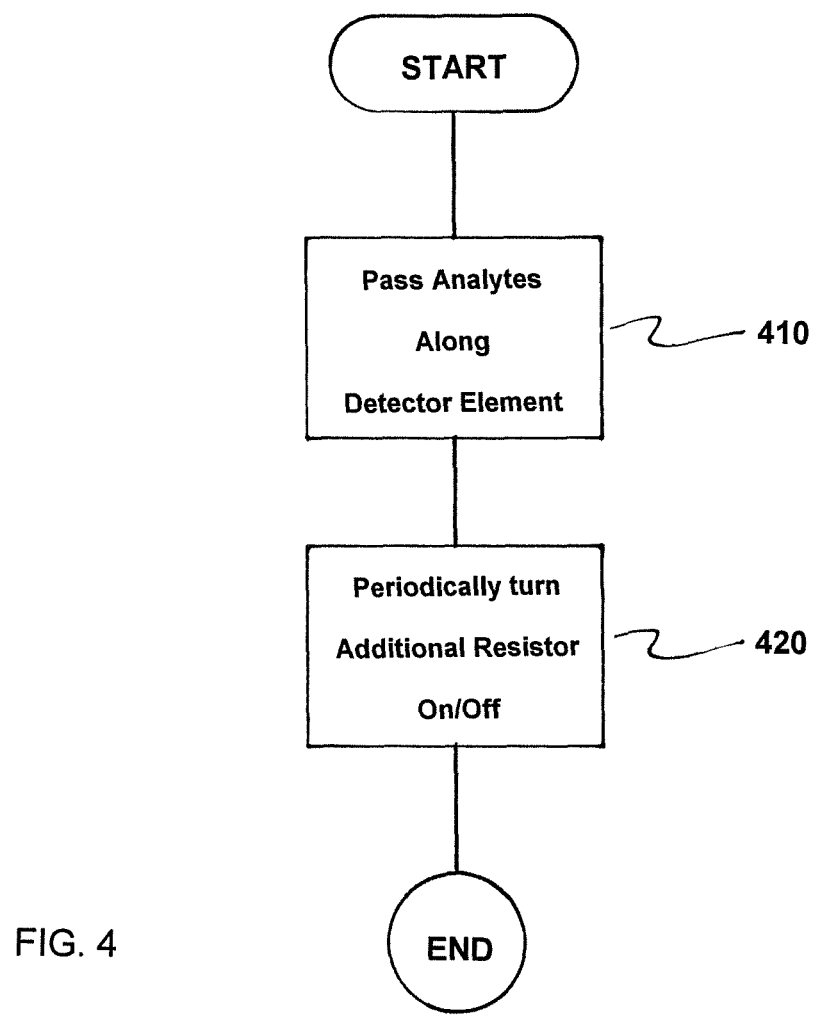
FIG. 4 is a flowchart of the method in accordance with the invention.

FIG. 4 is a flowchart of the method for operating a thermal conductivity detector in accordance with the invention. The method comprises passing a flow of analytes eluting from a chromatography column along a heatable resistive detector element, as indicated in step 410. In accordance with the invention, the detector element is electrically arranged together with resistors in separate arms of a measuring bridge and the measuring bridge being powered by an amplifier that detects the differential voltage between two opposite nodes of the measuring bridge and applies an output voltage to other opposite nodes of the measuring bridge to maintain the heatable resistive detector element at a constant operating temperature. Next, an additional resistor in one arm of the measuring bridge is periodically turned on and off at a predetermined duty cycle and at a period lower than the thermal time constant of the detector element to adjust an operating temperature of the heatable resistive detector element, as indicated in step 420.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed:

1. A thermal conductivity detector for a gas chromatograph comprising:
    a heatable resistive detector element configured to be physically arranged in a flow of analytes eluting from a chromatography column and electrically arranged with resistors in separate arms of a measuring bridge;
    an additional resistor with a controllable switch in parallel and connected in series with the heatable resistive detector element or a resistor in one arm of the measuring bridge;
    an amplifier configured to detect a differential voltage between two opposite nodes of the measuring bridge and to apply an output voltage to other opposite nodes of the measuring bridge to maintain the heatable resistive detector element at a constant operating temperature; and
    a controller configured to provide a control signal to the switch to adjust the operating temperature;
    wherein the control signal is a pulse-width modulated voltage with a period lower than a thermal time constant of the detector element.

2. The thermal conductivity detector of claim 1, wherein the pulse-width modulated voltage has a momentary change in duty cycle at characteristic times-of-arrival of predetermined ones of the flow of analytes at the detector element.

3. The thermal conductivity detector of claim 1, wherein the controllable switch is connected at one end to one of the other opposite nodes of the measuring bridge.

4. The thermal conductivity detector of claim 1, wherein the heatable resistive detector element is connected at one end to one of the other opposite nodes of the measuring bridge.

5. The thermal conductivity detector of claim 1, wherein the switch is a semiconductor device.

6. The thermal conductivity detector of claim 5, wherein the semiconductor device is a transistor selected from the group consisting of a bipolar transistor and a field effect transistor.

7. The thermal conductivity detector of claim 5, further comprising:
    a second switch coupled in series with the controllable switch, the controllable and second switches being controlled together; and
    a voltage divider connected between the other opposite nodes of the measuring bridge, a tap of said voltage divider being coupled to a node between the serially coupled controllable and second switches, and the voltage divider being configured to provide a tap voltage having a level which corresponds to a voltage drop across the additional resistor.

8. The thermal conductivity detector of claim 6, further comprising:
    a second switch coupled in series with the controllable switch, the controllable and second switches being controlled together; and
    a voltage divider connected between the other opposite nodes of the measuring bridge, a tap of said voltage divider being coupled to a node between the serially coupled controllable and second switches, and the voltage divider being configured to provide a tap voltage having a level which corresponds to a voltage drop across the additional resistor.

9. The thermal conductivity detector of claim 7, wherein the tap of said voltage divider is coupled to the node between the controllable and second switches via a buffer.

10. A gas chromatograph comprising at least one thermal conductivity detector of claim 1.

* * * * *